United States Patent [19]
Kowalczykowski et al.

[11] Patent Number: 5,747,247
[45] Date of Patent: May 5, 1998

[54] SPECTROSCOPIC HELICASE ASSAY

[75] Inventors: Stephen C. Kowalczykowski; Angela K. Eggleston, both of Davis, Calif.

[73] Assignee: The Regents of The University of California, Oakland, Calif.

[21] Appl. No.: 280,020

[22] Filed: Jul. 25, 1994

[51] Int. Cl.$^6$ .............................. C12Q 1/68; C12P 19/34
[52] U.S. Cl. ........................ 435/6; 424/941; 356/328; 435/91.1
[58] Field of Search .................... 435/6, 91.1; 424/94.1; 356/328

[56] References Cited

PUBLICATIONS

Houston et al, (Jun. 1994), "Spectrophotometric assay for enzyme–mediated unwinding of double–stranded DNA", Proc. Natl. Acad. Sci. 91:5471–5474.

Trieu et al, (1989), "Identification of *Escherichia coli* DNA helicase IV with the use of a DNA helicase activity gel," J. Bacteriol. 171:2128–2135.

George et al, (1992), "Inhibition of DNA helicase II unwinding and ATPase activities by DNA–interacting ligands", J. Biol. Chem. 267:10683–10689.

Raney et al, (1994), "A fluorescence based assay for monitoring helicase activity" Proc. Natl. Acad. Sci. 91:6644–6648.

Bjornson et al, (1994), "Single–turnover kinetics of helicase–catalyzed DNA unwinding monitored continuously by fluorescence entergy transfer", Biochemistry 33:14306–16.

Runyon et al, (1993), "Overexpression, purification, DNA binding, and dimerization of the *Escherichia coli* uvrD gene product (Helicase II)", Biochemistry 32:602–612.

Kapuscinski et al, "Interactions of nucleic acids with fluorescent dyes: Spectral properties of condensed complexes", J. Histochem. Cytochem. 38(9):1323–1329, Sep. 1990.

Korangy et al, "A mutation in the consensus ATP–binding sequence of the RecD subunit reduces the processivity of the RecBCD enzyme from *Escherichia coli*", J. Biol. Chem. 267(5):3088–3095, Feb. 1992.

Eggleston et al., "A Helicase Assay Based on the Displacement of Fluorescent Nucleic Acid Binding Ligands", Genetic Recombination and Genome Rearrangements, Copper Mountain, Colorado (Jul. 25–30) (Abstract).

Higuchi et al., "Kinetic PCR Analysis: Real–time Monitoring of DNA Amplification Reactions", *Bio/Technology* 11:1026–1030 (1993).

Higuchi et al., "Simultaneous Amplification and Detection of Specific DNA Sequences", *Bio/Technology* 10:413–417 (1992).

Roman and Kowalczykowski, "Characterization of the Adenosinetriphosphatase Activity of the *Escherichia coli* RecBCD Enzyme: Relationship of ATP Hydrolysis to the Unwinding of Duplex DNA", *Biochemistry* 28:2873–2881 (1989).

Roman and Kowalczykowski, "Characterization of the Helicase Activity of the *Escherichia coli* RecBCD Enzyme Using a Novel Helicase Assay", *Biochemistry* 28:2863–2873 (1989).

*Primary Examiner*—W. Gary Jones
*Assistant Examiner*—Jeffrey Fredman
*Attorney, Agent, or Firm*—Richard Aron Osman

[57] ABSTRACT

The invention provides spectroscopic methods for detecting helicase activity and inhibitors of helicase activity. Samples are assayed for helicase activity by: (a) incubating a mixture of the sample, double-stranded nucleic acid and a suitable luminescent marker which lumineses selectively in the presence of double-stranded nucleic acid; (b) exposing the mixture to light capable of inducing luminescence from the marker; and (c) detecting the intensity of luminescence from the mixture. Alternatively, samples are assayed for helicase inhibitors by further including in the mixture a helicase and incubating the mixture under conditions whereby, but for the presence of an inhibitor of the helicase in the sample, the helicase would be capable of converting a portion of the double-stranded nucleic acid into single-stranded nucleic acid. In both assays, helicase activity is inversely proportional to the detected luminesense. The methods are particularly suited to high-throughput drug screening.

18 Claims, 7 Drawing Sheets

FIG 2A1
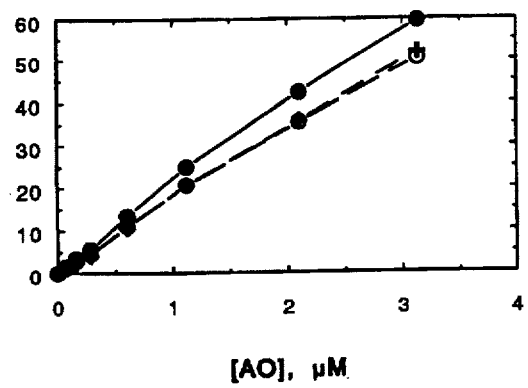
FIG 2A2
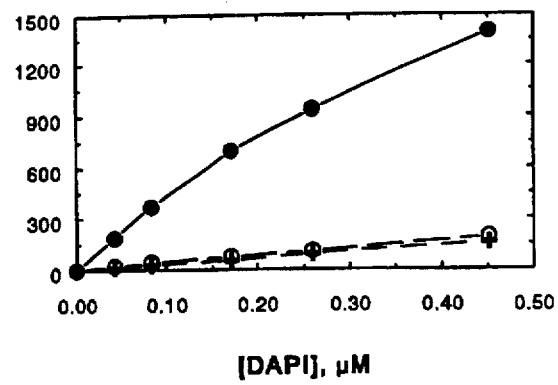
FIG 2A3
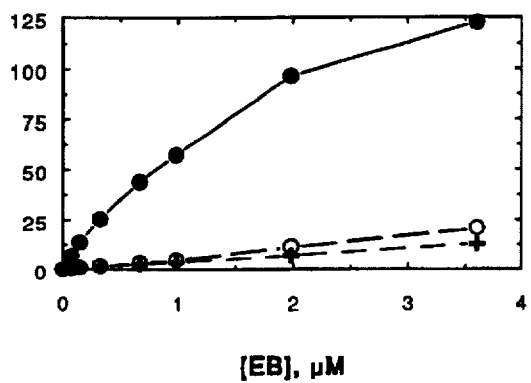
FIG 2A4
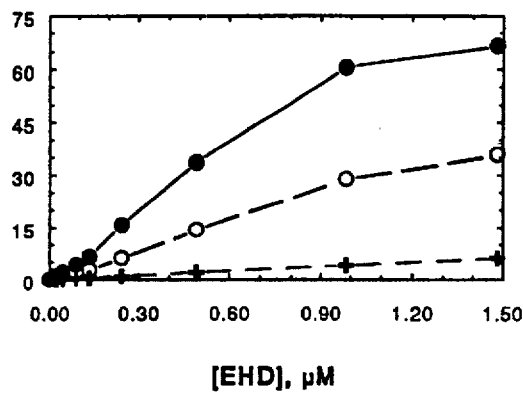
FIG 2A5
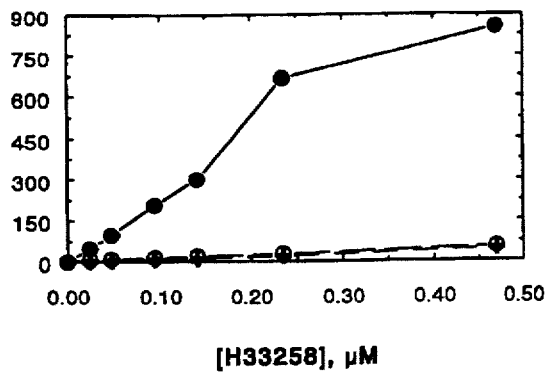
FIG 2A6
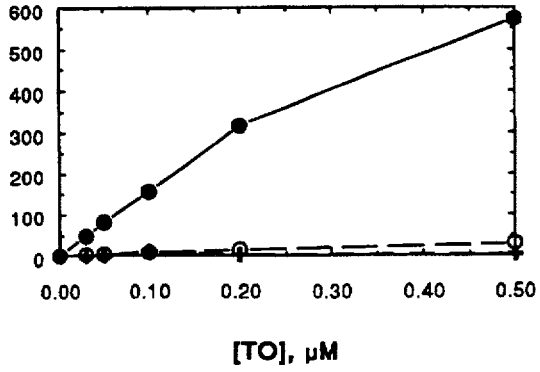

SPECTROSCOPIC HELICASE ASSAY

The research carried out in the subject application was supported in part by grants from the National Institutes of Health. The government may have rights in any patent issuing on this application.

INTRODUCTION

1. Field of the Invention

The field of this invention is assays for helicase activity and assays screening for drugs which interfere with helicase activity.

2. Background

Helicases are enzymes which unwind double-helical nucleic acids, usually in an NTP-dependent manner. Cellular, microbial, phage, and viral helicases are involved in a wide variety of cellular functions including DNA replication, recombination, and repair and RNA transcription, translation, and processing. Because of the critical functions played by helicases, they provide promising targets for therpeutic intervention, e.g. in pathogenic infection. For example, many infectious diseases, especially fungal and viral disease, have resisted efforts to identify effective pharmaceutical therapies.

Identifying and developing new pharmaceuticals is a multibillion dollar industry in the U.S. alone. Especially needed are efficient methods of identifying pharmacological agents or drugs which are active against pathogens which have hitherto defied effective therapy. If amenable to automated, cost-effective, high throughput drug screening, assays for specific helicase inhibitors would have immediate application in a broad range of domestic and international pharmaceutical and biotechnology drug development programs.

Several types of helicase assays have been developed: measuring the sensitization of labeled duplex DNA to single-strand specific nucleases, electron microscopy, displacement of a labeled fragment which is annealed to a single-stranded DNA or RNA molecule, and more recently, a spectrophotometric assay that utilizes a ssDNA binding protein as the reporter molecule. Unfortunately, each of the assays described above has limitations which restrict their applicability to high-throughput drug screening: they are slow, expensive and/or require considerable manipulation.

Relevant Literature

Roman and Kowalczykowski (1989) Biochemistry 28, 2863–2873 describes a helicase assay exploiting the intrinsic fluorescence of *E. coli* SSB protein that is quenched when the protein binds single-stranded DNA.

Higuchi et al. (1992) Bio/technology 10, 413–417 and Higuchi et al. (Sep. 11, 1993) Bio/technology 11, 1026–1030 describe an assay for monitoring of PCR by detecting ethidium bromide fluorescence.

George et al. (1992) J Biological Chem 267, 10683–10689 compares the inhibition of DNA helicase I, II and IV and Rep protein by several DNA binding drugs.

Eggleston et al. (1993) Abstract, "Genetic Recombination and Genome Rearrangements", Copper Mountain, Colo. (Jul. 25–30)

SUMMARY OF THE INVENTION

The invention provides spectroscopic methods for detecting helicase activity and inhibitors of helicase activity. Specific helicase inhibitors provide pharmacological agents useful in the treatment of disease.

Assaying a sample for helicase activity according to the invention involves: (a) incubating a mixture of a sample, an initial amount of double-stranded nucleic acid, and a marker which is capable of luminesence proportional to the concentration of double-stranded nucleic acid in the mixture; (b) exposing the mixture to light capable of inducing luminescence from the marker; (c) detecting the intensity of the luminescence from the mixture; wherein the difference between the initial and the final amount of double-stranded nucleic acid, as determined by luminescence intensity, correlates with the helicase activity of the sample.

Assaying a sample for the presence of a helicase inhibitor involves: (a) incubating a mixture of a sample, a helicase and, as above, an initial amount of double-stranded nucleic acid and a luminescent marker, under conditions whereby, but for the presence of an inhibitor of the helicase in the sample, the helicase would be capable of converting a control portion of the initial amount of double-stranded nucleic acid into single-stranded nucleic acid; (b) exposing the mixture to light capable of inducing luminescence from the marker; (c) detecting the intensity of the luminescence from the mixture; wherein a difference between the initial and the final amount of double-stranded nucleic acid less than the control portion indicates the presence of an inhibitor of helicase activity in the sample.

A wide variety of alternative embodiments of the general method are disclosed, including a variety of markers, nucleic acids, helicases, etc. The methods are particularly suited to high-throughput drug screening. In addition, the invention provides kits for drug screening based on the disclosed methods.

BRIEF DESCRIPTION OF THE FIGURE

FIGS. 2A1–2A6 and 2B. Fluoresecence enhancement of dyes in the presence of ds- and ssDNAs.

DETAILED DESCRIPTION OF THE INVENTION

Figure 1A:
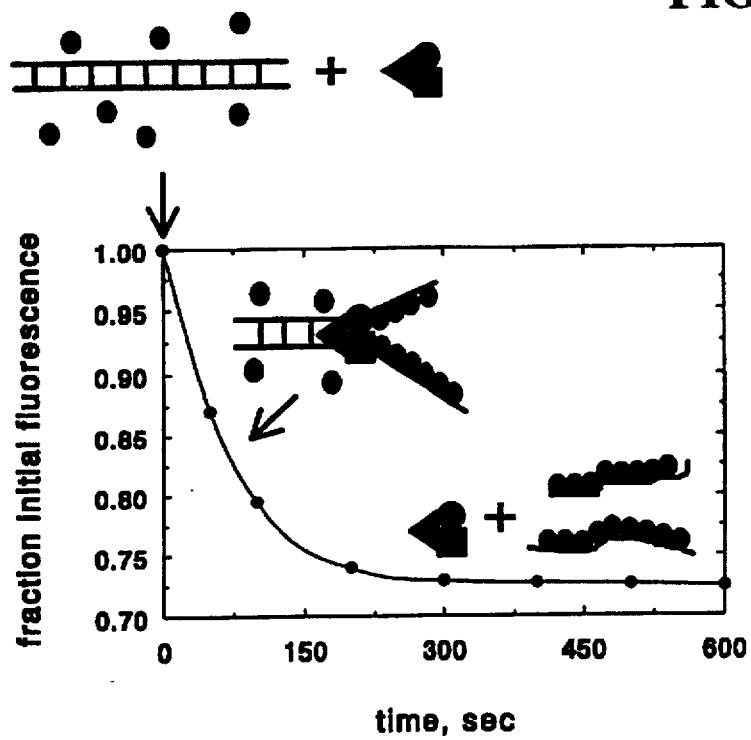
FIGS. 1A and 1B. Illustration of the SSB protein fluorescence and dye displacement assays used to measure DNA helicase activity.

The invention provides efficient spectroscopic methods for detecting helicase activity and identifying inhibitors of helicase activity. Specific helicase inhibitors provide pharmacological agents useful in the diagnosis or treatment of disease. The methods are amenable to automated, cost-effective high throughput drug screening and have immediate application in a broad range of domestic and international pharmaceutical and biotechnology drug development programs. In addition, the invention provides kits for helicase inhibitor screening which include premeasured amounts of the compositions used in the disclosed methods.

Since helicases are necessary for a wide variety of cellular functions including growth, target diseases are limited only in that disease or disease progression be subject to inhibition by interference with the activity of one or more specific helicases. As such, target diseases include viral, bacterial and fungal infections, metabolic disease, genetic disease, cell growth and regulatory disfunction, such as neoplasia, inflammation, hypersensitivity, etc. The target diseases may be afflictions of plants, especially agricultural crops, or animals, especially livestock, house animals and humans.

Assaying for helicase activity or for inhibitors of helicase acitivity initially involves incubating a mixture comprising a sample, a known initial amount of double-stranded nucleic acid comprising hybridized complementary single-stranded nucleic acid, a luminescent marker and, in the case of the inhibitor assay, a helicase. Except as noted below, the process parameters for each method are the same.

As used herein, the articles "a" and "an" mean one or more; hence, by "a helicase" is meant to include assays which simultaneously screen for inhibitors of several helicases.

The selection of the luminescent marker and assay conditions including marker concentration are critical considerations. To provide the requisite spectrophotometric properties, the marker generally has one or more absorbtion and emission peaks that do not coincide with absorbtion or emission peaks of other components of the mixture, particularly the nucleic acid and protein. Hence, the marker generally has an absorbtion peak at greater than about 200 nm, preferably not between 275 and 285 if significant 280 nm absorbing protein is present in the mixture, and less than about 800 nm, to facilitate use of commercially available and cost-effective markers and instrumentation.

The marker must provide a detectable luminescence, preferably fluorescence, intensity in the presence of the double-stranded nucleic acid. This luminescence is at least 3-fold, preferably at least 10-fold, more preferably at least 30-fold and most preferably at least 100-fold greater than the luminescence of a comparable double-stranded nucleic acid composition without the marker. The marker must also provide greater luminescent intensity in the presence of the double-stranded nucleic acid than in the presence of a molar-equivalence of constituent unhybridized complementary single-stranded nucleic acid, i.e. greater intensity when the complementary strands are hybrizided than when they are separated. Generally, the marker provides at least a 3-fold, preferably at least a 5-fold, more preferably at least a 7-fold, most preferably at least a 10-fold luminescent intensity enhancement in the presence of the double stranded nucleic acid.

As discussed below, preferred markers provide minimal interference with helicase activity. Markers which satisfy the requisite spectrophotometric properties, double-stranded nucleic acid binding selectivity and helicase compatibilty include a wide range of structures. Exemplary markers are described below. Additional preferred properties for marker selection include cost-effectiveness and commercial availability, quantum yield, non-toxicity, etc.

The marker is provided at a concentration within a concentration range within which the measured activity of assayed helicase(s) (or in the case of an assay for helicase activity, one or more control helicases) is independent of marker concentration. At excessive marker concentration, the opportunity for interference with helicase activity is increased. Hence, marker concentration is minimized. On the other hand, at excessively low marker concentration, emission intensity is reduced and the opportunity of lag artifact (described below) is enhanced. Hence, the marker concentration is at least sufficient to provide the requisite emission intensity and to avoid lag behavior. For many suitable markers, the effective concentration range is frequently from about 1 nM to 1 uM, preferably between 10 and 600 nM, more preferably between 150 and 400 nM. However, the concentrations necessary to avoid lag behavior and inhibition are dependent on other incubation components and conditions and is determined empirically for a given marker and incubation conditions, using the guidelines and methods described below.

The assay mixture also comprises a known initial amount of double-stranded nucleic acid. The initial amount of double-stranded nucleic acid is selected to provide a detectable depletion of double-stranded nucleic acid if helicase activity is present in the assay. The double stranded nucleic acid is usually linear DNA or RNA, though circular plasmids or other nucleic acids or structural analogs may be substituted so long as helicase activity can be measured. In some applications, supercoiled DNA provides optimal activity. The nucleic acid may be of any length amenable to the assay conditions and requirements. Typically the nucleic acid is between 10 bp and 50 kb, preferably between about 20 bp and 20 kb, more preferably between about 40 bp and 10 kb. Preferred concentrations are greater than the Km of the subject helicase, frequently greater than about one nM (nucleic acid molecule).

The nucleic acid may be of any sequence which provides a convenient substrate for the helicases. Generally, restriction fragments of conventiently replicated vectors provide an inexpensive source of double-stranded nucleic acid substrate. The assays are generally compatible with the presence of DNA binding proteins, such as histones.

For the helicase inhibitor assay, it is advantageous to include a variety of potential substrates, e.g. double-stranded nucleic acides of varied size, sequence, protein complexing, etc. to improve the likelihood of detecting substrate-sensitive helicases.

The helicase used in the inhibitor assay is selected based on the target application. Rapidly growing cells (e.g. in neoplasia) may be targeted by inhibitors of human helicases, especially replicative helicases. In addition, pathogen-selective or -specific helicases are used to identify pharmacological therapeutics for the treatment of infectious disease. Fungal, viral and parasitic helicases, in particular, provide medically urgent targets for identifying inhibitors by the subject methods.

The helicase may be purifed from a natural source or may be recombinant and is usually provided in at least a partially-purified form. Often only a portion of the native helicase is used in the assay, the portion being sufficient for helicase activity not less than an order of magnitude less than that of the full-length helicase. Portions capable of imparting the requisite binding specificity and affinity are readily identified by those skilled in the art. A wide variety of molecular and biochemical methods are available for generating catalytic portions, see e.g. Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, New York, N.Y., 1992) or that are otherwise known in the art.

The sample used in the helicase activity assay is typically a cellular or nuclear extract. This assay provides a convenient means of identifying target helicases for the inhibitor assay. In the inhibitor assay, the sample is generally a preselected candidate helicase inhibitor or, especially for high-throughput drug screening, a library-derived candidate agent. Preferred preselected candidates are known phosphatase and kinase inhibitors as many human helicases are regulated by phosphorylation. Library-derived candidate agents encompass numerous chemical classes, though typically they are organic compounds; preferably small organic compounds. Small organic compounds have a molecular weight of more than 50 yet less than about 2,500, preferably less than about 1000, more preferably, less than about 500. Candidate agents comprise functional chemical groups necessary for structural interactions with proteins and/or DNA, and typically include at least an amine, carbonyl, hydroxyl or carboxyl group, preferably at least two of said functional chemical groups, more preferably at least three. The candidate agents often comprise cyclical carbon or heterocyclic structures and/or aromatic or polyaromatic structures substituted with one or more of the forementioned functional groups. Candidate agents are also found among biomolecules including peptides, saccharides, fatty acids, steroids, purines, pyrimidines, derivatives, structural analogs or combinations thereof, and the like.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogs.

In addition, the mixture usually includes additional reagents, such as salts, buffers, etc. to facilitate helicase activity. Also, reagents that otherwise improve the efficiency of the assay, such as protease inhibitors, nuclease inhibitors, antimicrobial agents, single-stranded DNA binding protein (SSB, below), etc. may be used.

For the helicase assay, the resultant mixture is incubated under conditions under which one or more control helicases would be capable of converting at least a detectable portion of the initial amount of double-stranded nucleic acid into unhybridized complementary single-stranded nucleic acid, whereby a final amount of the double-stranded nucleic acid remains (i.e. results or is formed). The selection of the control helicase (or panel comprising a range of different control helicases) provides a positive control to insure that helicase activity, if present in the sample, will be detectable. Hence, controls are selected to maximize the likelihood of encompassing an activity functionally similar, in terms of the subject assay, to that sought to be detected in the sample.

For the helicase assay, by detectable portion is meant that the assay conditions are such that for positive control helicases, the luminescent intensity of the inital amount of double-stranded nucleic acid would be detectably greater, and repeatably so, as measured by the subject assay, than the final amount. For the helicase inhibitor assay, the mixture is incubated under conditions whereby, but for the presence of an inhibitor of the helicase in the sample, that (or those) helicase would be capable of converting a control portion of the initial amount of double-stranded nucleic acid into unhybridized complementary single-stranded nucleic acid, whereby a final amount of the double-stranded nucleic acid is formed. The control portion is a defined detectable portion from which inhibition is determined.

In both assays, incubations may be performed at any temperature which facilitates activity as measured by luminescent intensity, typically between 4° and 40° C., more commonly between 15° and 40° C. Incubation periods are likewise selected for optimal activity but also minimized to facilitate rapid, high-throughput screening. Typically, incubation times range between 10 sec. and 60 min., preferably less than 30 min., more preferably less than 15 min.

After or during the incubations, the mixture is exposed to light capable of inducing luminescence from the marker. This excitation light may be provided by any convenient source, though preferred sources minimize the band-width of the incident light to limit absorbtion of mixture components other than the marker, e.g. filtered or laser (e.g. nitrogen laser) light. Following excitation, the intensity of the luminescence from the mixture at one or more wavelengths which correspond to emission peaks of the selected marker is measured by any convenient means, typically an instrument detector such as a fluorimeter.

In both assays, the intensity of the luminescence from the mixture correlates with the final amount of double-stranded nucleic acid in the mixture. In the helicase assay, the difference between the initial and the final amount of double-stranded nucleic acid correlates with the helicase activity of the sample. In the inhibitor assay, a difference between the initial and the final amount of double-stranded nucleic acid less than the control portion indicates the presence of an inhibitor of helicase activity in the sample. Candidate agents shown to selectively inhibit target helicase activity provide valuable reagents to the pharmaceutical and agricultural industries for cellular, plant, field crop, animal and human trials.

A wide variety of alternative embodiments of the general method are disclosed, including a variety of markers, nucleic acids, helicases, etc. The methods are particularly suited to automated high throughput drug screening. In a preferred embodiment, the individual sample incubation volumes are less than about 500 ul, preferably less than about 250 ul, more preferably less than about 100 ul. Such small sample volumes minimize the use of often scarce candidate agent and expensive or scarce helicases and markers. Furthermore, the methods provide for automation, especially computerized automation. Accordingly, the method steps are preferably performed by a computer-controlled electromechanical robot.

The following examples are offered by way of illustration and not by way of limitation.

EXAMPLES

Helicases serve a variety of functions in DNA metabolism (for reviews, see (1, 2)). Cellular (E. coli dnaB, priA, and rep proteins), phage (T4 gene 41 and dda proteins; T7 gene 4 protein), and viral (SV40 T antigen; HSV-1 UL5/UL52 complex and UL9 protein) helicases are involved in the initiation of replication, by unwinding DNA so that other proteins of the replication complex can assemble on the ssDNA. These proteins also participate in the elongation phase of replication, by unwinding the duplex DNA ahead of this complex to provide the required template. Other helicases (e.g., the E. coli recBCD and recQ proteins) are implicated in recombination by genetic criteria. In vitro, recBCD enzyme helicase activity generates the ssDNA substrate to which the recA protein of E. coli can bind to initiate heteroduplex DNA formation (3, 4). In addition, helicases such as the *E. coli* ruvAB complex may function in recombination to promote branch migration of recombination intermediates (5). Another class of helicases includes the *E. coli* uvrAB and uvrD, Saccharomyces cerevisiae Rad3 and Rad25, and human ERCC-2, -3, and -6 proteins (reviewed in (6)). These helicases act in nucleotide excision repair (7, 8) or methyl-directed mismatch repair (9) during both pre-incision (recognition of DNA damage or alteration) and post-incision (displacement of damaged fragment) steps. Various aspects of RNA metabolism are also dependent upon the action of helicases (for review, see (10)). The unwinding of RNA templates is required in processes as diverse as transcription termination (11), translation initiation (12, 13), and RNA processing (14–16).

Several types of assays have been developed to measure the unwinding of duplex nucleic acids by helicases. The first assays measured the sensitization of labeled duplex DNA to single-strand specific nucleases such as S1 or exonuclease I, a result of the production of ssDNA during unwinding (17–20). Electron microscopy was also employed to visualize directly the regions of DNA unwound by proteins such as recBCD enzyme, rep protein, *E. coli* helicases I and II, and SV40 T antigen (21–25). Currently, the most common assay measures the ability of a helicase to displace a labeled fragment which is annealed to a single-stranded DNA or RNA molecule; this displacement is detected by polyacrylamide gel electrophoresis, as a band which has altered mobility (26, 27). Finally, a continuous spectrophotometric assay that was developed for studies of recBCD enzyme helicase activity utilizes a ssDNA binding protein, either *E. coli* SSB protein (single-strand DNA binding protein) or phage T4 gene 32 protein, as the reporter molecule (28). As the dsDNA is unwound, the SSB protein binds to the ssDNA formed, resulting in quenching of its intrinsic fluorescence.

Each of the assays described above has merits and limitations. While the first three assays have the advantage that they are direct, they are non-continuous and require considerable manipulation before results are obtained. Also, the fragment displacement assay is predicated on the assumption that the displaced oligonucleotide will not reanneal. The SSB protein fluorescence assay overcomes several of these limitations because the easily measurable decrease in fluorescence provides a continuous signal, so that kinetic studies are more feasible. Second, annealing of unwound DNA is prevented, due to the binding of SSB protein. Also, the length of the duplex region is virtually unconstrained, allowing the detailed study of highly processive helicases (29). One disadvantage of this assay, however, is that the requirement for SSB protein obviates its use with helicases that require a ssDNA region to initiate unwinding and that therefore may be inhibited by the presence of ssDNA binding proteins.

We disclose here an assay which affords the advantages of the SSB fluorescence assay but which does not require the use of a DNA binding protein, namely, the use of fluorescent dyes as reporter molecules for the unwinding of duplex DNA and RNA. (Models illustrating the two types of assays are shown in FIG. 1.) Many chromophores have the property of enhanced fluorescent quantum yield when they are bound to nucleic acids relative to that observed when they are free in solution. In addition, this effect is generally greater when the dye molecules are bound to double-stranded, rather than single-stranded, substrates. Most well-characterized fluorescent probes for nucleic acids, such as DAPI and H33258, act by binding in the minor groove and display some sequence specificity, particularly if the sites are contiguously positioned (30, 31). Other intercalating dyes, such as TO, demonstrate no sequence specificity (32). Thus, we reasoned that it would theoretically be possible to monitor the process of DNA or RNA unwinding by measuring the decrease in fluorescence as the dye ligands are displaced from the duplex molecule. Such an assay would allow measurement of unwinding in the absence of additional components (e.g., SSB protein) which might otherwise interfere with the unwinding activity of certain helicases.

We have examined a variety of fluorophores including AO, acridine orange; DAPI, bis-benzimide; EB, ethidium bromide; EHD, ethidium homodimer; H33258, Hoechst 33258; and TO, thiazole orange, to determine their utility as reporter molecules in a continuous helicase assay. Extensive studies of several of these dyes (DAPI, H33258, and TO), which share the properties of having relatively low fluorescence in the presence of ssDNA and significant fluorescence enhancement upon binding to dsDNA, are describe below. The presence of these dyes has little effect on the activity of the recBCD helicase. The assay was characterized with regard to variation in dye, protein, and salt concentration, as well as temperature. Finally, the effect of SSB protein on the assay was examined.

EXPERIMENTAL PROCEDURES

Materials

Nucleic acids: pBR322 DNA was prepared by alkaline lysis and double-banding in CsCl-EB density gradients (34). Phage M13 ssDNA was prepared according to standard procedures (35). Nucleotide concentrations were determined at 260 nm using extinction coefficients of 6500 and 8784 $M^{-1}$ $cm^{-1}$ for ds- and ssDNA, respectively.

Proteins: RecBCD enzyme was purified as previously described (28, 36) and was quantitated at 280 nm using an extinction coefficient of $4 \times 10^5$ $M^{-1}$ $cm^{-1}$ (28). The specific activity of the enzyme preparation was $3.1 \times 10^5$ nuclease units/mg protein (37) and $4.2 \times 10^4$ helicase units/mg protein (28); its apparent binding stoichiometry was 3 molecules/end (28). SSB protein was purified as described (38) and was quantitated using an extinction coefficient of $3 \times 10^4$ $M^{-1}$ $cm^{-1}$ at 280 nm (39).

Fluorophores: EB was purchased from Sigma. AO, DAPI, EHD, H33258, and TO were obtained from Molecular Probes (Eugene, Oreg.). TO was obtained from Becton Dickinson. Each dye, except TO, was dissolved as a concentrated stock solution (~5 mg/ml) in water, and serial dilutions were made from this stock. TO was dissolved as a concentrated stock solution (~2 mg/ml) in 100% DMF (N, N dimethyl formamide); serial dilutions were made from this into TO dilution buffer (10% DMF, 0.1 mM 2-mercaptoethanol) to keep the dye soluble. Dye concentrations were determined in water using the stated extinction coefficients (given in $M^{-1}$ $cm^{-1}$): AO, $65 \times 10^3$ at 488 nm; DAPI, $33 \times 10^3$ at 345 nm; EB, $5.5 \times 10^3$ at 546 nm; EHD, $8.9 \times 10^3$ at 528 nm. The concentrations of H33258 and TO were determined in methanol using extinction coefficients of $46 \times 10^3$ and $77 \times 10^3$ $M^{-1}$ $cm^{-1}$ at 344 and 502 nm, respectively.

Methods

Fluorometric helicase assay: The standard reaction buffer consisted of 25 mM Tris-acetate (pH 7.5), 1 mM $Mg(OAc)_2$, and 1 mM DTT. When SSB protein was included, it was present at a 3-fold molar excess, assuming a site size of 15 nucleotides/monomer under stoichiometric conditions. This corresponds to a protein concentration which is 20% of the DNA (nucleotide) concentration. The DNA substrate was BamHI-digested pBR322 DNA, at a concentration of 10 uM nucleotide (2.1 nM ends).

The reaction (350 ul total volume) contained standard buffer, linear pBR322 DNA, and the indicated concentration of recBCD enzyme. (For each series of experiments in which the concentration of TO was varied, an appropriate amount of TO dilution buffer was added to the reaction so that the final concentration of DMF was constant ($\leq 0.3\%$). This was necessary because control experiments showed that DMF quenched fluorescence significantly.) SSB protein was added at this point for dye fluorescence measurements. The fluorescence signal due to these components was zeroed out. The fluorophore (either SSB protein or dye) was then added, and the reaction was allowed to equilibrate to the indicated temperature. Unwinding was initiated by the addition of ATP to 3 mM final concentration. Under these conditions (i.e., ATP in excess of $Mg^{2+}$ ion), the dsDNA exonuclease activity of recBCD enzyme is largely suppressed (36, 40). For SSB protein fluorescence measurements, the value for 100% unwinding was calculated as described previously (28, 41). For dye fluorescence experiments, the value for complete unwinding was obtained by subtracting the fluorescence in the presence of an equimolar amount of ssDNA (i.e., heat-denatured pBR322) ($F_{ssDNA}$) from the fluorescence at the start of the reaction ($F_{dsDNA}$). The difference in these values ($F_{dsDNA} - F_{ssDNA}$) was taken to be the maximum fluorescence change possible if all of the DNA molecules were fully unwound ($F_{exp}$). The observed fluorescence change ($F_{obs}$) was divided by this difference to obtain the extent of unwinding. Initial rates were then calculated as described previously (28).

Fluorescence measurements were carried out on a Shimadzu RF5000U spectrofluorophotometer. When the intrinsic fluorescence of SSB protein was measured, the excitation and emission wavelengths were set at 290 and 340 nm, respectively. The excitation and emission wavelengths for the various dyes were determined experimentally in the presence of dsDNA. For AO, these values were 487 and 510 nm; for DAPI, 345 and 467 nm; for EB, 546 and 590 nm; for EHD, 552 and 596 nm; for H33258, 344 and 487 nm; and for TO, 504 and 528 nm. When SSB protein fluorescence was monitored, the band widths were 1.5 and 10 nm for the excitation and emission slits, respectively; for all of the dye fluorescence experiments, these values were 5 and 10 nm, respectively.

RESULTS

Figure 1B:
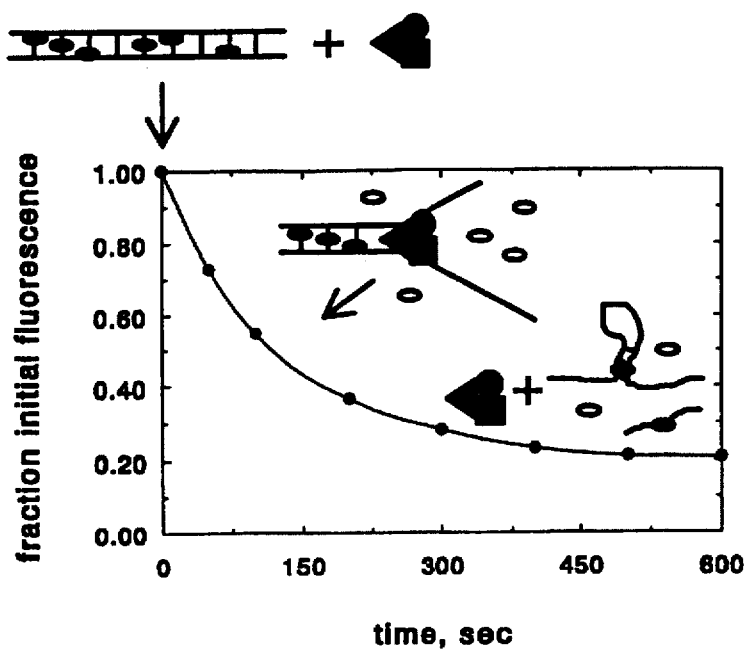

FIGS. 1A and B. illustrates the SSB protein fluorescence and dye displacement assays used to measure DNA helicase activity. In panel A is shown the SSB protein fluorescence assay developed by Roman and Kowalczykowski (28). In this assay, the fluorescent signal at the start of the reaction is high due to the intrinic fluorescence of SSB protein which is free in solution (filled circles). As the duplex DNA is unwound by a helicase (e.g., recBCD enzyme (circle/square/triangle)), SSB protein binds to the ssDNA formed, which results in partial quenching of its intrinsic fluorescence (stippled circles). This fluorescence decrease is easily measured. In the dye displacement assay (panel B), the dye molecules are initially bound to the duplex DNA (filled ovals), which enhances their fluorescence. As the dsDNA is unwound, the dye molecules are displaced. Regardless of whether the molecules exist free in solution (open ovals) or rebind to the ssDNA (stippled ovals), little fluorescence is produced. Thus, in this assay, fluorescence also decreases as the DNA is unwound, but in this case the fluorescence signal originates with the dsDNA substrate rather than the ssDNA product.

For helicase activity to be detected, dyes must exhibit relative enhancement of fluorescence upon binding dsDNA when compared to that obtained when the fluorophore is either in solution or bound to ssDNA. Although each dye displays greater fluorescence in the presence of dsDNA when compared to that in the presence of ssDNA, the fluorescent quantum yield and the dsDNA-specific enhancement are dependent upon the dye used (FIGS. 2A1–2A6). A dye titration was performed to determine both the magnitude of the unwinding signal (i.e., how much fluorescence is emitted in the presence of dsDNA as compared to that either in the presence of ssDNA or when free in solution) and the useful range of dye concentration. Titrations of dye were carried out at 20° C. in standard buffer (25 mM Tris-acetate (pH 7.5), 1 mM $Mg(OAc)_2$, 1 mM DTT) with 3 mM ATP. The dsDNA was 10 uM (nucleotide) linear pBR322 DNA, and the ssDNA was 10 uM (nucleotide) heat-denatured linear pBR322 DNA or M13 viral DNA. In panels A1–6, the dye fluorescence in the absence of DNA (+) or in the presence of ssDNA (o) or dsDNA (●) is shown. To determine the maximal dsDNA-specific enhancement of fluorescence, the ratio of the fluorescence in the presence of dsDNA to that in the presence of ssDNA was calculated (panel B).

In FIGS. 2A1–2A6, a wider separation in the values for dsDNA and those for ssDNA or free ligand indicates that there will be greater discrimination between the dsDNA substrate and ssDNA products. In the graph for AO, for example, the signal difference with this dye is small (i.e., only ~15% of the initial fluorescence signal can be lost as a result of unwinding). For TO, the signal from ssDNA-bound ligands is greater than for AO, but this fact is offset by a much greater increase in the fluorescence in the presence of dsDNA.

Figure 2B:
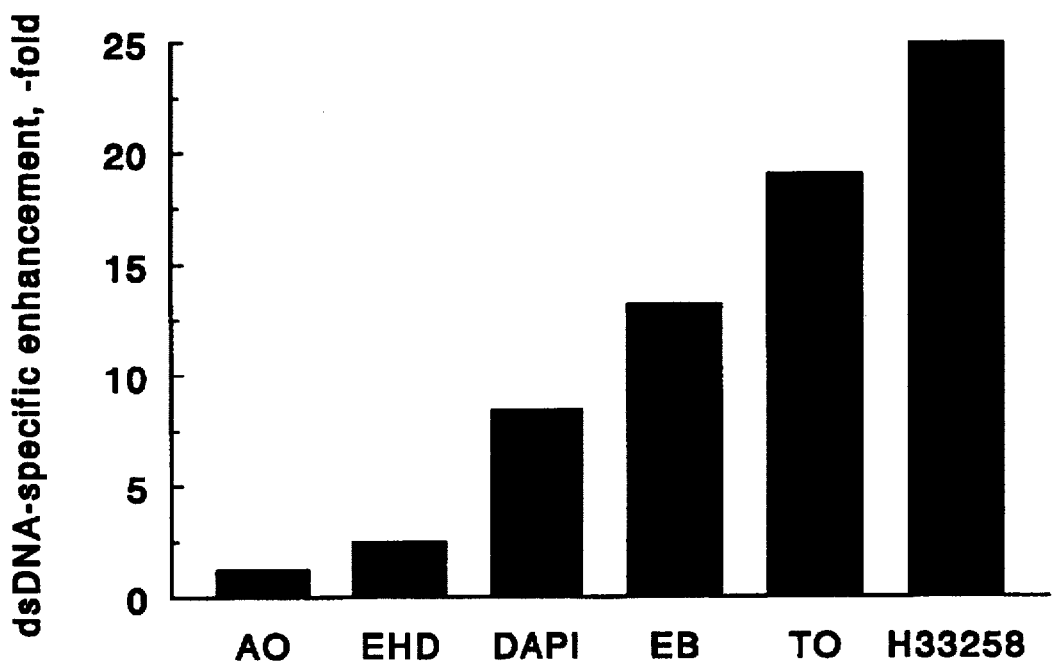

For helicase assays, not only is the absolute fluorescence yield a factor, but the fluorescence enhancement specific for dsDNA relative to ssDNA is also important. This parameter was calculated by dividing the fluorescence in the presence of dsDNA by that in the presence of ssDNA at the concentration of dye which maximized this difference (FIG. 2B). As is readily seen, H33258 displays the greatest dsDNA specificity relative to ssDNA, followed by TO, EB, and DAPI. Due to their specificity for dsDNA, strong fluorescence signal, and minimal fluorescence in the absence of DNA, the fluorophores DAPI, H33258, and TO were selected for further study. Our experiments indicate that EB also provides a useful reporter molecule.

Figure 3A:
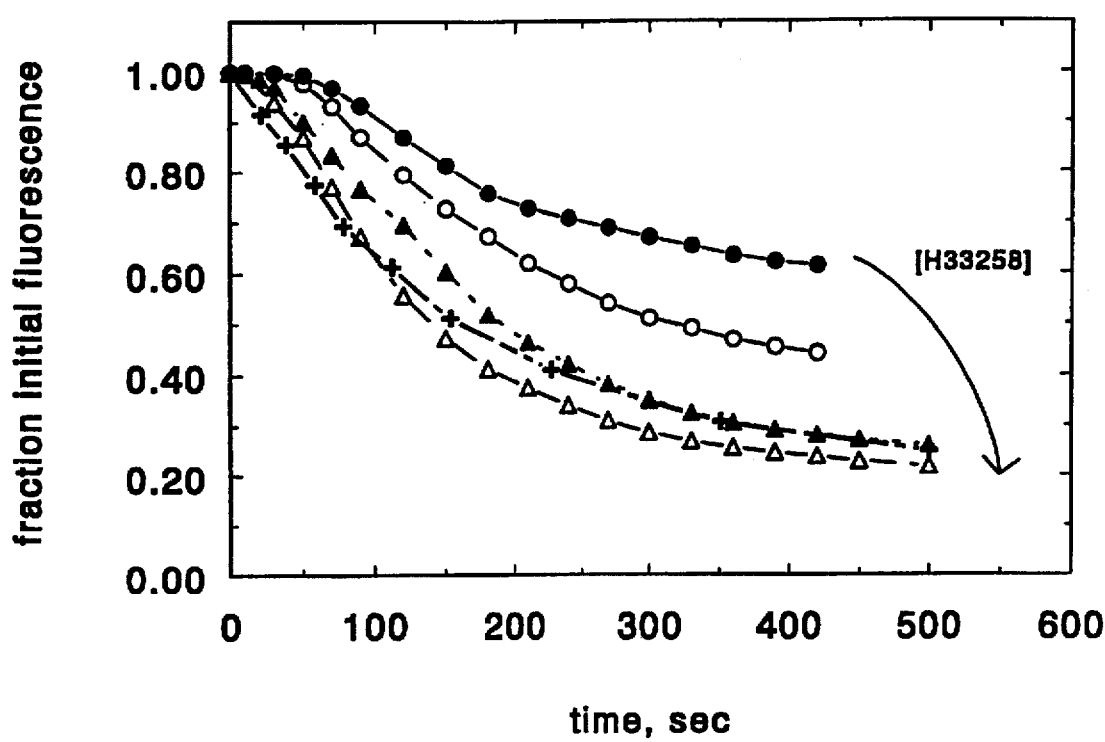
FIGS. 3A and 3B. Rate of DNA unwinding as a function of dye concentration.
Figure 4A:
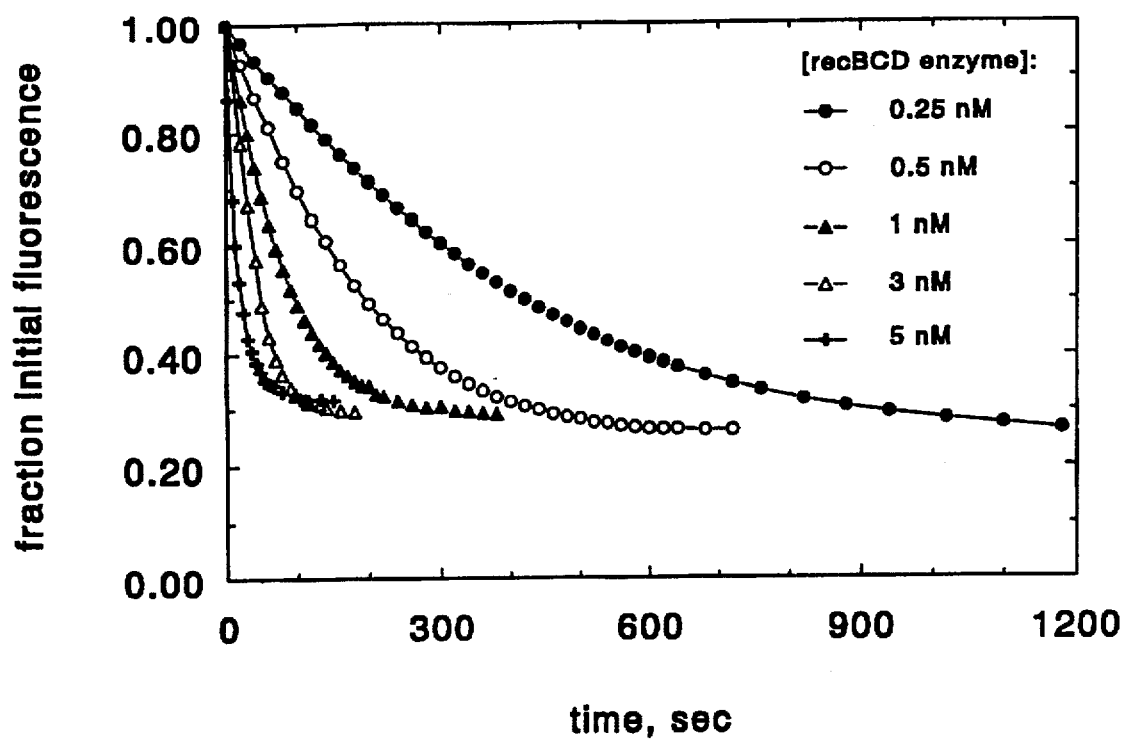
FIGS. 4A and 4B. Effect of fluorescent dyes on the $V_{max}$ and on the apparent DNA binding stoichiometry of recBCD enzyme.

Initial experiments indicated that DNA unwinding could be monitored using the signal produced by the binding of fluorescent dyes to duplex DNA (examples of typical unwinding traces are shown in FIGS. 3A and 4A). To determine whether the presence of dyes affected the observed rate of unwinding, the reaction (including SSB protein) was performed at several concentrations of DAPI, H33258, and TO. The reactions were performed at 20° C. in standard buffer with 10 uM nucleotide (2.1 nM ends) linear pBR322 DNA, 2 uM SSB protein, 0.5 nM total (0.17 nM functional) recBCD enzyme, and the indicated concentration of dye. Unwinding was initiated by adding ATP to a final concentration of 3 mM. For DAPI and H33258, reactions at low concentrations of dye displayed lag behavior; an example of these data using H33258 are shown in panel A. The concentration of H33258 was (in nM): 10 (●), 25 (o), 50 (▲), 100 (Δ), and 150 (+). For each dye (DAPI (●), H33258 (o), or TO (▲), the initial rate of unwinding was determined as described in the Experimental Procedures and is plotted in panel B as a function of dye concentration. Due to the lag behavior illustrated in panel A, the data at concentrations $\leq 100$ nM are considered unreliable, as indicated by shading this portion of the graph.

Unwinding reactions in the presence of either DAPI or H33258 (but not TO) display lag behavior at the lowest concentrations of dye (≦100 nM; data from a H33258 titration are shown in FIG. 3A); at or above 100–150 nM dye, lag behavior is not observed. We believe that the lag behavior at low dye concentration is due to redistribution of the relatively few displaced dye molecules to vacant binding sites in regions of duplex DNA which have not been unwound. The apparent extent of unwinding (i.e., the fraction of the observed fluorescence change) is reduced at very low dye concentrations; this is not attributable to binding of dye molecules to the walls of the cuvette, for example, because the addition of dye at either the beginning or the end of the reaction results in the same fluorescence signal. For example, the rebinding of a single dye molecule to regions of secondary structure in ssDNA may contribute a greater percentage of the total fluorescence under these conditions than at higher dye concentrations (see FIG. 3A). At higher dye concentrations (≧50 nM), however, the extent of measured DNA unwinding is independent of dye concentration (FIG. 3A).

Figure 3B:
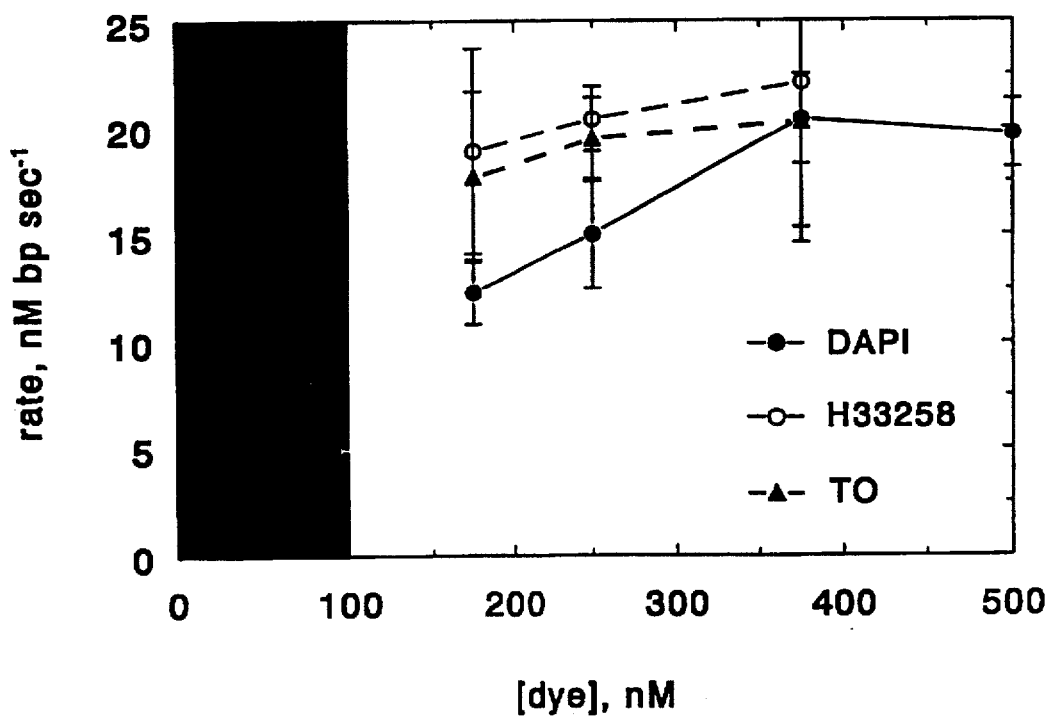

By normalizing the observed fluorescence changes to those obtained with heat-denatured controls, the observed rates of DNA unwinding can be determined. Plots of the observed unwinding rate as a function of dye concentration are shown in FIG. 3B. For all three dyes, the apparent rate increases somewhat as the dye concentration is increased but then appears to level off at value of 20–25 nM bp/s (at ~150 nM for H33258 and TO and 375 nM for DAPI). Because of the lag behavior and possible rebinding artifact described above, the data at concentrations below 100 nM do not reflect the true rate of unwinding and are not shown (indicated in FIG. 3B by shading). In subsequent experiments, we utilized concentrations of these dyes which are as low as possible without being affected by lag behavior.

RecBCD enzyme helicase activity demonstrates saturation behavior with regard to DNA concentration. The apparent rate of unwinding increases with enzyme concentration until all of the dsDNA ends present are saturated with active enzyme (28). The protein concentration at which saturation is achieved can be used to determine the apparent binding stoichiometry (i.e., the number of enzyme molecules/end), defined as the concentration of protein just at saturation divided by the concentration of DNA ends in the reaction. If the presence of fluorophores does not affect the interaction of recBCD enzyme with the ends of the DNA substrate, this value should be invariant.

Figure 4B:
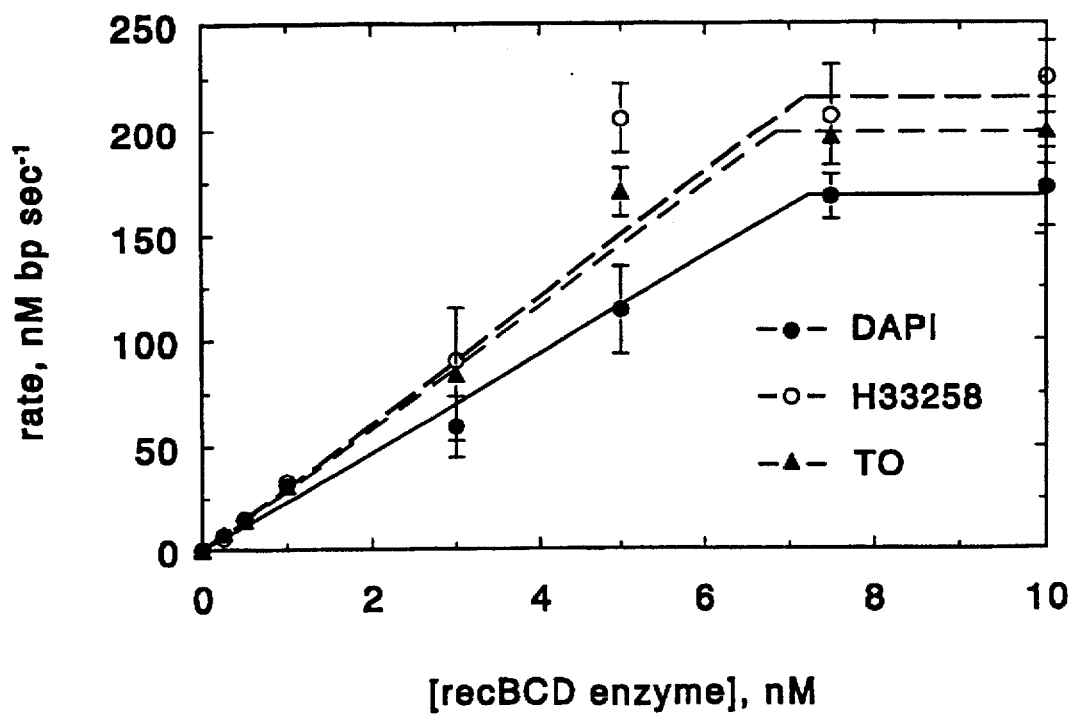

In FIG. 4A, raw data from an experiment in which recBCD enzyme concentration was varied at a given concentration of TO are shown; SSB protein was included to allow comparison to previous results. From results such as these, using either DAPI, H33258, or TO, the data in FIG. 4B were generated. Unwinding was performed as in FIG. 3, except that the concentration of recBCD enzyme was varied, and a constant concentration of fluorophore (250 nM for DAPI; 100 nM for H33258; and 300 nM for TO) was used. In panel A, a portion of the raw data obtained with TO are shown. The observed rates of unwinding derived from such experiments are shown in panel B. DAPI, ●; H33258, o; TO, ▲.

As is readily apparent, the enzyme concentration at which the reaction saturates does not vary significantly among the dyes. For DAPI, saturation is achieved at a protein concentration of 7.1 nM. Given that the concentration of DNA ends in the reaction is 2.1 nM, this corresponds to an apparent binding stoichiometry of 3.4±0.3 enzyme molecules/end.

Similarly, protein titrations using H33258 and TO yield apparent binding stoichiometries of 3.3±0.3 and 3.2±0.2 molecules/end, respectively. For comparison, the SSB protein fluorescence assay yields an apparent binding stoichiometry of 2.9±0.2 molecules/end. Thus, dye molecules bound to the substrate do not affect the apparent binding stoichiometry of recBCD enzyme.

Enzyme titrations also yield $V_{max}$ for unwinding in the presence of each dye. The value obtained using the SSB protein fluorescence assay is 250±25 nM bp/s. For DAPI, H33258, and TO, the observed rate of unwinding under these conditions is 180±20, 221±25, and 211±15 nM bp/s, respectively. However, because the DAPI and H33258 reactions were performed at dye concentrations which gave less than maximal rates of unwinding (see FIG. 3B), the values for these dyes are underestimates. When optimal concentrations of these dyes were used (400 nm DAPI; 300 nm H33258), the rates are, within experimental error, equal to those obtained using the SSB protein fluorescence assay. Thus, at 20° C., the $k_{cat}$ for DNA unwinding is approximately 65 bp unwound/functional enzyme molecule/s and is about 25% less than that determined by the SSB fluorescence assay.

Since the measurement of unwinding rates at saturating concentrations of enzyme is subject to variability, even at 20° C., due to the rapid rates of unwinding, the result that the inclusion of these dyes, particularly DAPI and H33258, did not substantially affect unwinding was confirmed by performing the reactions at low enzyme concentration, in the presence or absence of dye, and monitoring the apparent rate of unwinding by the SSB protein fluorescence assay. The addition of H33258 to a final concentration of 100 or 250 nM does not affect the observed rate of unwinding, whereas the addition of TO has a slight effect (<20% decrease at 250 nM dye; Table 1). These results indicate that, under experimentally defined optimal conditions, small DNA ligands do not impair the ability of a helicase to unwind DNA.

TABLE I

Effect of fluorescent dyes on DNA unwinding as measured by the SSB protein fluorescence assay.

| SSB protein | Fluorescent dye | Rate (nm bp/s) |
|---|---|---|
| + | none | 40.7 ± 4.1 |
| + | H33258 (100 nM) | 36.1 ± 4.5 |
| + | H33258 (250 nM) | 35.5 ± 1.9 |
| + | TO (100 nM) | 35.6 ± 1.3 |
| + | TO (250 nM) | 31.9 ± 0.7 |

The unwinding reaction was performed at 20° C. in buffer containing 25 mM Tris-acetate (pH 7.5), 1 mM Mg(OAc)$_2$, 3 mM ATP, 1 mM DTT, 10 uM nucleotide BamHI-digested pBR322 DNA, 2 uM SSB protein, 0.5 nM total (0.17 nM functional) recBCD enzyme, and the indicated concentrations of dye. SSB protein fluorescence was monitored.

Figure 5:
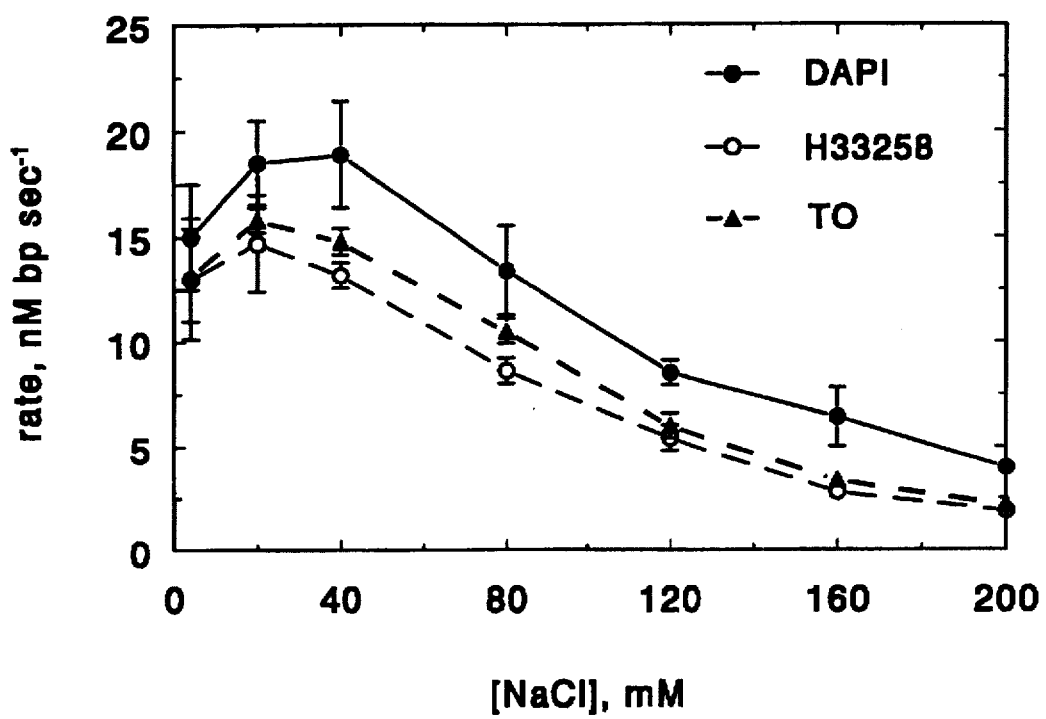
FIG. 5. Effect of NaCl concentration on the rate of unwinding by recBCD enzyme.

The $k_{cat}$ of the helicase activity of wild-type recBCD enzyme is slightly stimulated by concentrations of NaCl up to 60–100 mM; above this concentration, the activity declines with ~40% loss of activity in the presence of 200 mM NaCl (28, 41). Consequently, we also determined whether the salt sensitivity of the unwinding reaction catalyzed by recBCD enzyme is altered by the presence of the fluorescent dyes (FIG. 5). Reactions were again performed as in FIG. 3 except that NaCl was added to the indicated final concentration. The dye concentrations were: 250 nM for DAPI (●); 100 nM for H33258 (o); and 300 nM for TO (▲). The binding of the dye molecules to the DNA should not be significantly affected over this concentration range of salt; >50% of the DAPI circular dichroism signal is retained at 1M NaCl using native calf thymus DNA (31). The fluorescence signal was sensitive to the concentration of NaCl in the reaction, however, in agreement with previous studies on the effect of ionic strength on the binding and fluorescence quantum yield of DAPI and H33258 (31, 42). As expected for recBCD enzyme, the rate of unwinding increases with the addition of NaCl in the presence of the dyes; however, the salt optimum (~20–40 mM) is somewhat lower than that observed using SSB protein as the reporter molecule.

By performing the unwinding assay at different temperatures, the apparent energy of activation ($E_a$) can be determined. This parameter was determined for reactions containing DAPI, H33258, or TO in the presence of SSB protein. Using data derived from reactions performed at 20°, 25°, 32°, and 37° C., Arrhenius plots were generated. The slopes of these plots yield $E_a$ values of 12.7, 9.9, and 9.7 kcal/mole for DAPI, H33258, and TO, respectively. These values for H33258 and TO are similar or equivalent to that determined using the SSB fluorescence assay (9.7 kcal/mole; (28)), while that for DAPI is slightly greater. Thus, as expected from the results of the protein titrations, the presence of these ligands on the duplex DNA does not appear to significantly affect the ability of recBCD enzyme to denature the DNA substrate.

All of the assays presented above were performed in the presence of SSB protein so that the results could be directly compared to previous work. Under these conditions, SSB protein binds to the unwound strands and maintains their single-stranded character. When such reactions are examined by electron microscopy, the DNA is found to be in a "loop-tail" structure, with the tails being formed by the unwound strands which are bound by SSB protein (21). In the absence of SSB protein, the unwound strands can reanneal behind the enzyme, forming a "twin-loop" structure.

Figure 6A:
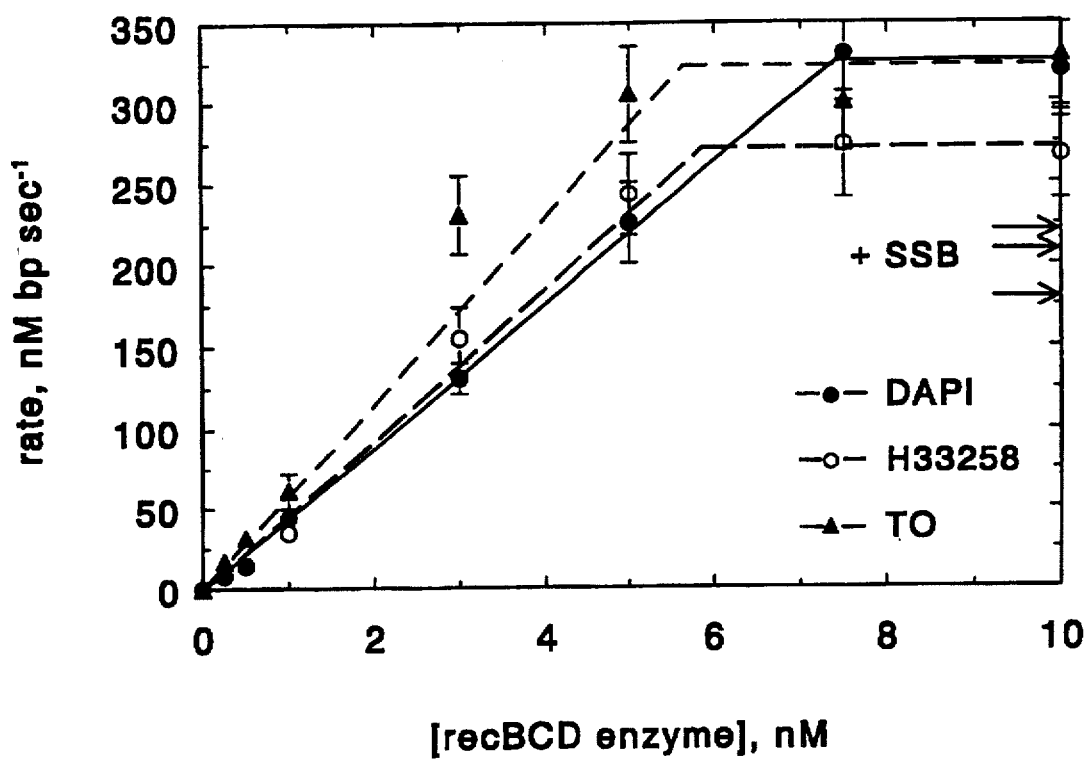
FIGS. 6A and 6B. Effect of SSB protein on the rate of unwinding by recBCD enzyme.

Previous studies addressing the effect of SSB protein on unwinding by recBCD enzyme utilized various non-continuous methods such as electron microscopy (21, 43), sucrose gradient sedimentation (44), and agarose gel electrophoresis (28). These methods did not detect a noticeable effect of SSB protein on the rate of unwinding by recBCD enzyme. The dye displacement assay has allowed us to approach this question using a continuous assay. An enzyme titration was performed in the absence of SSB protein to determine whether the observed rate of unwinding ($V_{max}$) and the binding stoichiometry were altered relative to those observed in its presence (FIG. 6A). For panel A, reactions were performed as described in the legend for FIG. 3 except that SSB protein was omitted; recBCD enzyme was added to the indicated final concentration. The concentrations of dyes used were: 250 nM for DAPI (●); 100 nM for H33258 (o); and 300 nM for TO (▲). An example of the reactions in the presence and absence of SSB protein is illustrated in panel B. The reactions contained 400 nM DAPI and the standard concentrations of the other components, with SSB protein (2 uM) as indicated. The value of the heat-denatured control for each condition is shown by the dashed horizontal lines.

In the DAPI reaction, the absence of SSB protein does not influence the apparent stoichiometry of binding to DNA ends by recBCD enzyme (3.5±0.1 molecules/end), although the observed $V_{max}$ is increased to 325±15 nM bp/s, a value 40% higher than in the presence of SSB protein. $V_{max}$ for both H33258 and TO is also increased by 25–50% (272±30 and 330±25 nM bp/s, respectively), while the binding stoichiometry in the presence of these two dyes is slightly lowered (2.8±0.3 and 2.7±0.2 molecules/end, respectively). This stoichiometry, however, is still consistent with the results from the SSB protein fluorescence assay.

Figure 6B:
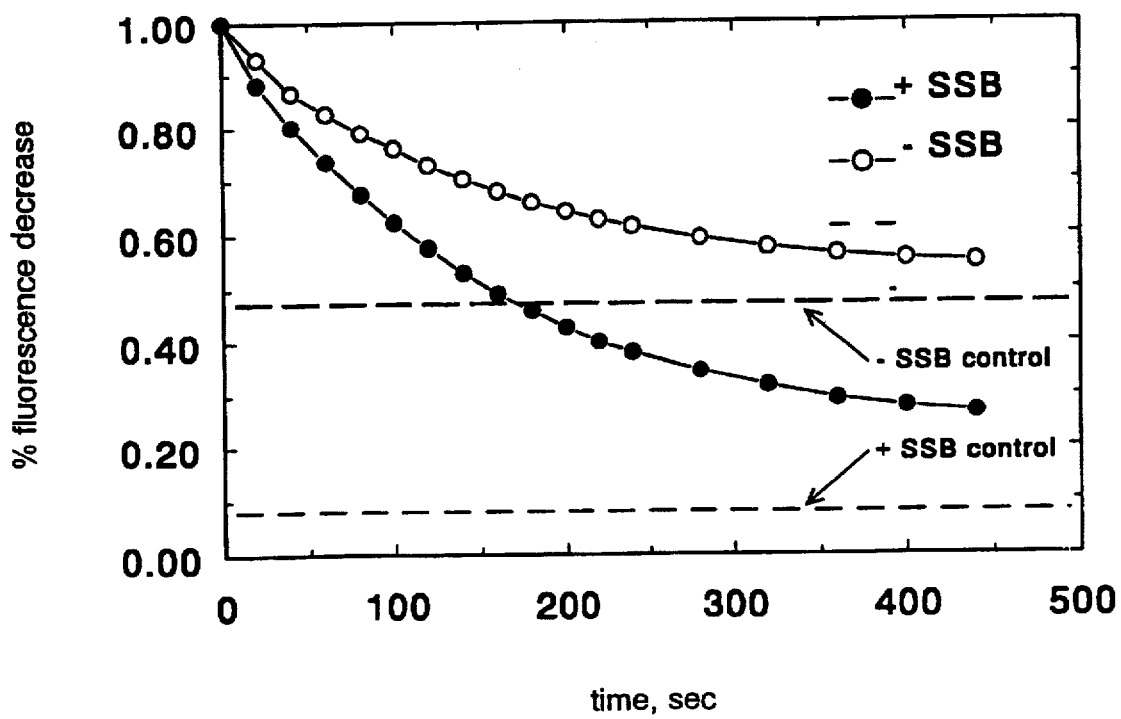

In the absence of SSB protein, the fluorescence of the heat-denatured ssDNA control is significantly greater than in its presence (an example is shown in FIG. 6B). Also, the observed fluorescence decrease of the unwinding reactions is less (FIG. 6B). These observations suggest that in the absence of SSB protein, the unwound DNA forms regions of secondary structure, and the binding of dye molecules to these regions results in greater fluorescence. This problem can apparently be overcome by including a ssDNA-specific nuclease, such as P1, throughout the reaction. Despite the differences in fluorescence signal, the apparent extent of unwinding in these reactions is only slightly changed, which would suggest that the DNA does not completely renature, as might be expected from the electron microscopic studies. Thus, it is possible that the binding of dye molecules to the ssDNA prevents its reannealing.

The subject assays have a wide application of uses in the measurement of the unwinding activity of a variety of helicases, regardless of their substrate requirements, provided that a suitable, non-inhibitory dye ligand is selected. Even if the presence of these ligands results in some inhibition of unwinding, it is possible to calibrate the dye displacement assay against another, more direct type of helicase assay. The assays are adaptable to helicases which require ssDNA tails, even when the concentration of duplex DNA and the number of high affinity binding sites (i.e., duplex DNA) is low, because the fluorescence enhancement of these dyes upon binding duplex nucleic acids is so great. Another advantage is that the effect of ssDNA binding proteins on unwinding reactions can be easily examined. While the reannealing of the unwound DNA strands in the absence of SSB protein posed a slight problem (<50%) using recBCD enzyme, the potential problem of DNA reannealing can be avoided by the addition of a ssDNA specific nuclease such as exonuclease I or P1 to digest the unwound strands and to prevent renaturation if necessary. Finally, this assay can be adapted to quantitate processivity measurements of helicase action. Specifically, such assays can be performed if a suitable trapping agent (e.g., heparin) is added to confine the fluorescent signal to the results of a single round of unwinding (45).

In our dye displacement assay, inhibition of the activity of the helicase under study by the dye ligands should be minimized. The fact that we obseved no significant inhibition of recBCD enzyme helicase activity in the presence of these dyes is consistent with studies using other DNA helicases recently reported by George et al. (33). They examined the effect of various DNA-interacting ligands on the ATPase and unwinding activity of several helicases, including E. coli helicase I, helicase II (uvrD), and rep proteins. In general, DNA-binding ligands which occupy the minor groove of duplex DNA, such as AO, DAPI, and H33258, did not greatly affect the activities (ATPase and helicase) of these enzymes ($K_i$~1–10 uM). However, the $K_i$ values determined by George et al. are significantly greater than the concentrations of dyes we have utilized in the dye displacement assay ($\leq$400 nM). On the other hand, ligands such as mitoxantrone, which not only intercalate but also position functional groups within the major groove of DNA, displayed potent but differential inhibition which was dependent upon both the ligand and the enzyme. Other studies have also observed inhibition of helicase activity by DNA ligands such as the antitumor drug CC-1065 (46, 47) and anthracycline antibiotics (48). Thus, the non-intercalating dyes DAPI, H33258, and TO are generally useful for the assay that we have described here.

The dye displacement assay also provides a new means by which the unwinding activity of RNA helicases can be examined. The measurement of RNA helicase activity has until now relied upon variations on the fragment displacement assay. Even though it is an intercalator, EB would not be expected to have an inhibitory effect, based upon the results of George et al. (33) and our observations. We have determined that EB, which has a high relative fluorescence enhancement (FIG. 2B), can be used to measure DNA unwinding. Since this type of intercalator binds to RNA in addition to DNA, RNA helicases are likewise amenable to this assay if an appropriate ligand, such as EB or propidium iodide, is utilized. Furthermore, the assay is also amenable to measure the degradation of duplex DNA by nuclease activity.

In conclusion, the dye displacement assay can be adapted for use with any helicase, whether it utilizes a DNA or RNA substrate, provided that a suitable, minimally-inhibitory nucleic acid binding dye is selected. An important parameter to optimize is the concentration of dye to be used; concentrations around 200–400 nM work best for a number of dyes. Within the effective marker concentration range, the dye displacement assay gives results which are consistent with those obtained from other types of helicase assays with far greater efficiency.

PARENTHETICAL REFERENCES

1. Matson, S. W., and Kaiser-Rogers, K. A. (1990) Annu. Rev. Biochem. 59, 289–329
2. Matson, S. W. (1991) in Progress in Nucleic Acid Research and Molecular Biology, Vol. 40, pp. 289–326, Academic Press, New York
3. Roman, L. J., Dixon, D. A., and Kowalczykowski, S. C. (1991) Proc. Natl. Acad. Sci. USA
4. Dixon, D. A., and Kowalczykowski, S. C. (1991) Cell 66, 361–371
5. Tsaneva, I. R., Mller, B., and West, S. C. (1993) Cell 69, 1171–1180
6. Hoeijmakers, J. H. J. (1991) J. Cell. Sci. 100, 687–691
7. Grossman, L., and Yeung, A. T. (1990) Mutat. Res. 236, 213–221
8. Lin, J. J., and Sancar, A. (1992) Molec. Microbiol. 6, 2219–2224
9. Modrich, P. (1989) J. Biol. Chem. 264, 6597–6600
10. Schmid, S. R., and Linder, P. (1992) Molec. Microbiol. 6, 283–292
11. Brennan, C. A., Dombroski, A. J., and Platt, T. (1987) Cell 48, 945–952
12. Rozen, F., Edery, I., Meerovitch, K., Dever, T. E., Merrick, W. C., and Sonnenberg, N. (1990) Mol. Cell. Biol. 10, 1134–1144
13. Jaramillo, M., Dever, T. E., Merrick, W. C., and Sonnenberg, N. (1991) Mol. Cell. Biol. 11, 5992–5997
14. Sachs, A. B., and Davis, R. W. (1990) Science 247, 1077–1079
15. Ripmaster, T. L., Vaughn, G. P., Woolford, J. L., Jr. (1992) Proc. Natl. Acad. Sci. USA 89, 11131–11135
16. Stepien, P. P., Margossian, S. P., Landsman, D., and Butow, R. A. (1992) Proc. Natl. Acad. Sci. USA 89, 6813–6817
17. Abdel-Monem, M., Durwald, H., and Hoffmann-Berling, H. (1976) Eur. J. Biochem. 65, 441–449
18. Duguet, M., Yarranton, G., and Gefter, M. (1979) Cold Spring Harbor Symp. Quant. Biol. 43, 335–343
19. Kuhn, B., Abdel-Monem, M., and Hoffmann-Berling, H. (1979) Cold Spring Harbor Symp. Quant. Biol. 43, 63–67
20. Palas, K. M., and Kushner, S. R. (1990) J. Biol. Chem. 265, 3447–3454
21. Taylor, A. F., and Smith, G. R. (1980) Cell 22, 447–457
22. Baumel, I. Meyer, T. F., and Geider, K. (1984) Eur. J. Biochem. 138, 247–251
23. Benz, I., Muller, H., Abdel-Monem, M., and Hoffman-Berling, H. (1986) Acta Microbiologica Polonica 35, 191–197
24. Runyon, G. T., Bear, D. G., and Lohman, T. M. (1990) Proc. Natl. Acad. Sci. USA 87, 6383–6387
25. Dodson, M, Dean, F. B., Bullock, P., Echols, H. and Hurwitz, J. (1987) Science 238, 964–967
26. Venkatesan, M., Silver, L. L., and Nossal, N. G. (1982) J. Biol. Chem. 257, 12426–12434
27. Matson, S. W., Tabor, S., and Richardson, C. C. (1983) J. Biol. Chem. 258, 14017–14024
28. Roman, L. J., and Kowalczykowski, S. C. (1989) Biochem. 28, 2863–2873
29. Roman, L. J., Eggleston, A. K., and Kowalczykowski, S. C. (1992) J. Biol. Chem. 267, 4207–4214
30. Kapuscinski, J., and Szer, W. (1979) Nucl. Acids Res. 6, 3519–3534
31. Manzini, G., Barcellona, M. L., Avitabile, M., and Quadrifoglio, F. (1983) Nucl. Acids Res. 11, 8861–8876
32. Glazer, A. N., and Rye, H. S. (1992) Nature 359, 859–861
33. George, J. W., Ghate, S., Matson, S. W., and Besterman, J. M. (1992) J. Biol. Chem. 267, 10683–10689
34. Sambrook, J., Fritsch, E. F., and Maniatis, T. (1989) Molecular Cloning: A Laboratory Manual, 2nd Ed., Cold Spring Harbor Laboratory, Cold Spring Harbor, N.Y.
35. Messing, J. (1983) Meth. Enzymol. 101, 20–78
36. Eggleston, A. K., and Kowalczykowski, S. C. (1993) J. Mol. Biol. 231, 605–620
37. Eichler, D. C., and Lehman, I. R. (1977) J. Biol. Chem. 252, 499–503
38. LeBowitz, J. (1985) Ph.D. Thesis, The Johns Hopkins University, Baltimore, Md.
39. Ruyechan, W. T., and Wetmur, J. G. (1976) Biochem. 15, 5057–5064
40. Dixon, D. A. (1993). Ph.D. Thesis, Northwestern University, Evanston, Ill.
41. Eggleston, A. K., and Kowalczykowski, S. C. (1993) J. Mol. Biol. 231, 621–633
42. Latt, S. A., and Stetten, G. (1976) J. Histochem. Cytochem. 24, 24–33
43. Telander-Muskavitch, K. M., and Linn, S. (1982) J. Biol. Chem. 257, 2641–2648
44. Mackay, V., and Linn, S. (1976) J. Biol. Chem. 251, 3716–3719
45. Korangy, F., and Julin, D. A. (1992) J. Biol. Chem. 267, 3088–3095
46. Maine, I. P., Sun, D., Hurley, L. H., and Kodadek, T. (1992) Biochem. 31, 3968–3975
47. Sun, D., and Hurley, L. H. (1992) J. Med. Chem. 35, 1773–1782
48. Bachur, N. R., Yu, F., Johnson, R., Hickey, R., Wu, Y., and Malkas, L. (1992) Molec. Pharmacol. 41, 993–998

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A continuous, kinetic spectroscopic method for detecting helicase activity in a sample, said method comprising the steps of:

(a) incubating a mixture comprising a sample, a known initial amount of double-stranded nucleic acid comprising hybridized complementary single-stranded nucleic acid, and a luminescent marker, wherein said marker is bound to said double stranded nucleic acid and present at a concentration whereby said marker is capable of at least 5-fold greater luminescent intensity in the presence of said double-stranded nucleic acid than in the presence of a molar-equivalence of unhybridized said complementary single-stranded nucleic acid, and said concentration is within a concentration range within which the measured activity of one or more control helicases is independent of marker concentration, under conditions under which one or more control helicases would be capable of converting at least a detectable portion of said initial amount of double-stranded nucleic acid into unhybridized said complementary single-stranded nucleic acid;

whereby a final amount of said double-stranded nucleic acid is formed;

(b) exposing said mixture to light capable of inducing luminescence from said marker;

(c) detecting the intensity of said luminescence from said mixture;

wherein the intensity of said luminescence from said mixture correlates with said final amount of double-stranded nucleic acid in said mixture and the difference between said initial and said final amount of double-stranded nucleic acid correlates with the helicase activity of said sample.

2. A continuous, kinetic spectroscopic method for detecting the presence of inhibitors of helicase activity in a sample, said method comprising the steps of:

(a) incubating a mixture comprising a sample, a helicase, a known initial amount of double-stranded nucleic acid comprising hybridized complementary single-stranded nucleic acid, and a luminescent marker, wherein said marker is bound to said double stranded nucleic acid and present at a concentration whereby said marker is capable of at least 5-fold greater luminescent intensity in the presence of said double-stranded nucleic acid than in the presence of a molar-equivalence of unhybridized said complementary single-stranded nucleic acid, and said concentration is within a concentration range within which the measured activity of one or more control helicases is independent of marker concentration, under conditions whereby, but for the presence of an inhibitor of said helicase in said sample, said helicase would be capable of converting a control portion of said initial amount of double-stranded nucleic acid into unhybridized said complementary single-stranded nucleic acid, whereby a final amount of said double-stranded nucleic acid is formed;

(b) exposing said mixture to light capable of inducing luminescence from said marker;

(c) detecting the intensity of said luminescence from said mixture;

wherein the intensity of said luminescence from said mixture correlates with said final amount of double-stranded nucleic acid in said mixture and a difference between said initial and said final amount of double-stranded nucleic acid less than said control portion indicates the presence of an inhibitor of helicase activity in said sample.

3. A method according to claim 1, wherein said at least 5-fold greater luminescent intensity is at least a 10-fold greater luminescent intensity.

4. A method according to claim 1, wherein said marker is a fluorescent dye.

5. A method according to claim 1, wherein said marker is a fluorescent dye and said concentration is between 150 and 400 nM.

6. A method according to claim 1, wherein said marker is Hoechst 33258 (H33258).

7. A method according to claim 1, wherein said marker is bis-benzimide (DAPI).

8. A method according to claim 1, wherein said marker is thiazole orange (TO).

9. A method according to claim 1, wherein said marker is ethidium bromide (EB).

10. A method according to claim 1, wherein said mixture further comprises a ssDNA specific nuclease to digest unwound strands and prevent renaturation.

11. A method according to claim 2, wherein said at least 5-fold greater luminescent intensity is at least a 10-fold greater luminescent intensity.

12. A method according to claim 2, wherein said marker is a fluorescent dye.

13. A method according to claim 2, wherein said marker is a fluorescent dye and said concentration is between 150 and 400 nM.

14. A method according to claim 2, wherein said marker is Hoechst 33258 (H33258).

15. A method according to claim 2, wherein said marker is bis-benzimide (DAPI).

16. A method according to claim 2, wherein said marker is thiazole orange (TO).

17. A method according to claim 2, wherein said marker is ethidium bromide (EB).

18. A method according to claim 2, wherein said mixture further comprises a ssDNA specific nuclease to digest unwound strands and prevent renaturation.

* * * * *